United States Patent [19]

Maier et al.

[11] Patent Number: 4,676,823
[45] Date of Patent: Jun. 30, 1987

[54] COMPOSITION FOR PROTECTING CULTIVATED PLANTS FROM THE PHYTOTOXIC ACTION OF HERBICIDES

[75] Inventors: Ludwig Maier, Arlesheim; Hans Moser, Magden, both of Switzerland

[73] Assignee: Ciba-Geigy Corporation, Ardsley, N.Y.

[21] Appl. No.: 817,216

[22] Filed: Jan. 8, 1986

Related U.S. Application Data

[62] Division of Ser. No. 598,952, Apr. 11, 1984, Pat. No. 4,579,691.

[30] Foreign Application Priority Data

Apr. 21, 1983 [CH] Switzerland .......................... 2150/83

[51] Int. Cl.⁴ ............................................ H01N 25/32
[52] U.S. Cl. .......................................... 71/86; 47/57.6; 71/118
[58] Field of Search ................................ 71/86; 47/57.6

[56] References Cited

FOREIGN PATENT DOCUMENTS 2322703 11/1974 Fed. Rep. of Germany.

*Primary Examiner*—Catherine L. Mills
*Attorney, Agent, or Firm*—Edward M. Roberts

[57] ABSTRACT

When applied as safeners, the haloacylaminoalkylphosphinates, haloacylaminoalkylphosphinates and haloacylaminoalkylphosphine oxides of the formula I below are able to protect cultivated plants from the phytotoxic effects of herbicides. Suitable crops are preferably sorghum, cereals, rice, maize and soya beans and the herbicides employed are chloroacetanilides and thiocarbamates.

The haloacylaminoalkylphosphonates, haloacylaminoalkylphosphinates and haloacylaminoalkylphosphine oxides have the formula I

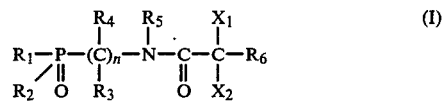

wherein
$R_1$ is $C_1$-$C_4$alkyl, $C_1$-$C_4$alkoxy, $C_2$-$C_4$alkenyloxy, $C_2$-$C_4$alkynyloxy, $C_1$-$C_4$haloalkyl, $C_2$-$C_8$alkoxyalkoxy or $C_1$-$C_4$cyanoalkoxy,
$R_2$ is hydrogen or a substitutent as defined for $R_1$,
$R_3$ and $R_4$ are each independently hydrogen, $C_1$-$C_4$alkyl or one of $R_3$ and $R_4$ is also a radical

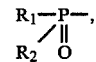

or both taken together with the carbon atom to which they are attached are also a $C_3$-$C_{11}$cycloalkyl radical,
$R_5$ is hydrogen, $C_1$-$C_4$alkyl, $C_3$-$C_7$cycloalkyl, $C_2$-$C_4$alkenyl, $C_2$-$C_4$-alkynyl, $C_2$-$C_8$alkoxyalkyl, $C_1$-$C_4$haloalkyl or aralkyl,
$R_6$ is hydrogen or $C_1$-$C_4$alkyl,
$X_1$ and $X_2$ are each independently halogen or one of $X_1$ and $X_2$ is also hydrogen, and
n is 1, 2 or 3.

11 Claims, No Drawings

COMPOSITION FOR PROTECTING CULTIVATED PLANTS FROM THE PHYTOTOXIC ACTION OF HERBICIDES

This is a divisional of application Ser. No. 598,952 filed on Apr. 11, 1984, now U.S. Pat. No. 4,579,691.

The present invention relates to a composition for protecting cultivated plants from the phytotoxic action of herbicides which contain a haloacylaminoalkylphosphonate, haloacylaminoalkylphosphinate or haloacylaminoalkylphosphine oxide as herbicide antagonist, and to compositions which, in addition to containing such an antagonist (also called antidote or safener), already contain the herbicide, and to a method of selectively controlling weeds, which comprises the use of a herbicide and said safener. The invention also relates to novel haloacylaminoalkylphosphonates, haloacylaminoalkylphosphinates and haloacylaminoalkylphosphine oxides and to the preparation thereof.

It is known that herbicides belonging to a very wide range of compound classes such as triazines, urea derivatives, carbamates, thiocarbamates, haloacetanilides, halophenoxyacetic acids etc., when employed in an effective concentration, often also damage cultivated plants to a certain extent in addition to the weeds which it is desired to control. Too high concentrations are often applied unintentionally and randomly whenever peripheral zones overlap on zonal spraying, whether as a consequence of the action of wind or through miscalculating the sweep of the spray device employed. The climatic conditions or the nature of the soil may be such that the concentration of herbicide reommended for normal conditions acts as an overdose. The quality of the seeds may also be a factor in the tolerance of the herbicide. To counteract this problem, different compounds have already been proposed which are able specifically to antagonise the harmful action of the herbicide on the cultivated plant, i.e. to protect the cultivated plant without noticeably influencing the herbicidal action on the weeds to be controlled. However, it has been found that the proposed antidotes very often have a species-specific activity both with respect to the cultivated plants and to the herbicide and also, in some cases, contingent on the mode of application, i.e. a specific antidote is often suitable only for a specific cultivated plant and a few classes of herbicides.

For example, British patent specification 1 277 557 describes the protective treatment of seeds or seedlings of wheat and sorghum with certain oxamic acid esters and amides against attack by "ALACHLOR" (N-methoxymethyl-N-chloroacetyl-2,6-diethylaniline). Antidotes for treating cereals, maize and rice seeds against the harmful effects of herbicidal thiocarbamates are proposed in German Offenlegungsschrift specifications 1 952 910 and 2 245 471 and in French patent specification 2 012 611. German patent specification 1 576 676 and U.S. Pat. No. 3,131,509 disclose the use of hydroxyaminoacetanilides and hydantoins for protecting cereal seeds from the effects of carbamates.

The direct pre- or postemergence treatment of certain useful plants with antidotes as antagonists of specific classes of herbicides in a crop area is disclosed in German Offenlegungsschrift specifications 2 141 586 and 2 218 097 and in U.S. Pat. No. 3,867,444.

Further, German Offenlegungsschrift 2 402 983 discloses that maize plants can be effectively protected against damage by chloroacetanilides by adding an N-disubstituted dichloroacetamide as antidote to the soil.

The haloacylaminoalkylphosphonates, haloacylaminoalkylphosphinates and haloacylaminoalkylphosphine oxides used as antagonists of herbicides have the formula I

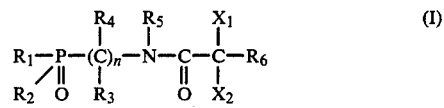

wherein
$R_1$ is $C_1$–$C_4$alkyl, $C_1$–$C_4$alkoxy, $C_2$–$C_4$alkenyloxy, $C_2$–$C_4$alkynyloxy, $C_1$–$C_4$haloalkyl, $C_2$–$C_8$alkoxyalkoxy or $C_1$–$C_4$cyanoalkoxy,
$R_2$ is hydrogen or a substituent as defined for $R_1$,
$R_3$ and $R_4$ are each independently hydrogen, $C_1$–$C_4$alkyl or one of $R_3$ and $R_4$ is also a radical

or both taken together with the carbon atom to which they are attached are also a $C_3$–$C_{11}$cycloalkyl radical,
$R_5$ is hydrogen, $C_1$–$C_4$alkyl, $C_3$–$C_7$cycloalkyl, $C_2$–$C_4$alkenyl, $C_2$–$C_4$alkynyl, $C_2$–$C_8$alkoxyalkyl, $C_1$–$C_4$haloalkyl or aralkyl,
$R_6$ is hydrogen or $C_1$–$C_4$alkyl,
$X_1$ and $X_2$ are each independently halogen or one of $X_1$ and $X_2$ is also hydrogen, and
n is 1, 2 or 3.

Alkyl by itself or as moiety of another substituent may be methyl, ethyl, n-propyl and isopropyl, and n-butyl, isobutyl, sec-butyl and tert-butyl. Examples of alkenyl radicals are vinyl, allyl, methallyl, butenyl and butadienyl. Examples of alkynyl radicals are ethynyl, propynyl and butynyl. Depending on the indicated number of carbon atoms, cycloalkyl radicals may be monocyclic or polycyclic radicals, e.g. cyclopropyl, cyclobutyl, cyclopentyl, cyclohexyl, cycloheptyl, cyclooctyl and bicyclo[2.2.1]heptyl, bicyclo[3.2.0]octyl and decahydronaphthyl radicals.

Aralkyl radicals comprise phenyl and naphthyl radicals which are linked through $C_1$–$C_4$alkyl. Aralkyl is preferably phenethyl and, most preferably, benzyl.

Halogen is fluorine, chlorine, bromine and iodine, with chlorine and bromine being preferred.

Effective safeners are halacylaminoalkylphosphonates of the formula I, wherein each of $R_1$ and $R_2$ is $C_1$–$C_4$alkoxy, each of $R_3$ and $R_4$ is hydrogen or methyl, $R_5$ is hydrogen, $C_1$–$C_4$alkyl or benzyl, $R_6$ is hydrogen, each of $X_1$ and $X_2$ is chlorine or one of $X_1$ and $X_2$ is also hydrogen, and n is 1; and also the haloalkylaminoalkylphosphinates of the formula I, wherein $R_1$ is $C_1$–$C_4$alkoxy, $R_2$ is $C_1$–$C_4$alkyl, each of $R_3$ and $R_4$ is hydrogen or methyl, $R_5$ is hydrogen, $C_1$–$C_4$alkyl or benzyl, $R_6$ is hydrogen, each of $X_1$ and $X_2$ is chlorine or one of $X_1$ and $X_2$ is hydrogen, and n is 1; or the haloacylaminoalkylphosphine oxides of the formula I, wherein $R_1$ is $C_1$–$C_4$alkyl, $R_2$ is hydrogen or $C_1$–$C_4$alkyl, each of $R_3$ and $R_4$ is hydrogen or methyl, $R_5$ is hydrogen, $C_1$–$C_4$alkyl or benzyl, $R_6$ is hydrogen, and each of $X_1$ and $X_2$ is chlorine or one of $X_1$ and $X_2$ is also hydrogen, and n is 1; and, in particular, the following compounds:
diethyl chloroacetylaminomethylphosphonate, diisopropyl chloroacetylaminomethylphosphonate,
diethyl dichloroacetylaminomethylphosphonate,
diisopropyl dichloroacetylaminomethylphosphonate,
diethyl bromoacetylaminomethylphosponate,
diisopropyl bromoacetylaminomethylphosphonate,
diethyl chloroacetylaminoprop-2-ylphosphonate,
diethyl chloroacetylbenzylaminoprop-2-ylphosphonate,
diethyl chloroacetylaminomethenediphosphonate,
diethyl chloroacetylaminocyclohex-1-ylphosphonate.

Many compounds of formula I are novel and others are known. For example, haloacylaminomethylphosphonates are described as flame retardants in DE-OS 2 322 703; and chlorinated acetyl-, propionyl- or butyrylaminomethylphosphonic acids and esters thereof are described as compounds for increasing the sucrose content of sugar cane in U.S. Pat. No. 3,961,934. Finally, the preparation of such haloacetyl- and halopropionylaminomethylphosphonates are intermediates for obtaining dihydro-2H-1,2,4-oxaphosphorin-5(6H)-one-oxides is described in Zhurnal Obshoei Khimii 37(9), 2061-5 (1967) [q.v. CA 68, 49686 w (1968) or 46(8), 1693-1698 (1976)].

Novel compounds are those of the formula I

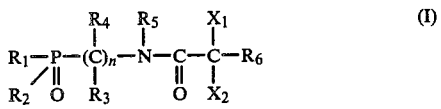

wherein $R_1$, $R_2$, $R_3$, $R_4$, $R_5$, $R_6$, $X_1$, $X_2$ and n are as defined above, with the proviso that $R_1$ and $R_2$ may not both be methoxy or ethoxy when n is 1, each of $R_3$, $R_4$ and $R_6$ is hydrogen, $R_5$ is hydrogen or methyl, each of $X_1$ and $X_2$ is chlorine or one of $X_1$ and $X_2$ is also hydrogen.

These novel compounds are prepared by reacting an aminoalkylphosphonate, aminoalkylphosphinate or aminoalkylphosphine oxide of the formula II

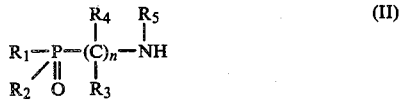

wherein $R_1$, $R_2$, $R_3$, $R_4$, $R_5$, and n have the meanings given above, with an equimolar amount of a haloacyl halide or haloacyl anhydride of the formula III

wherein Y is a halogen atom or a radical

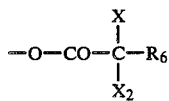

and $R_6$, $X_1$ and $X_2$ are as defined above, in a non-aqueous inert organic solvent and in the presence of an equimolar amount of an organic base, and isolating the condensation product from the reaction mixture.

The reaction is carried out in the temperature range from room temperature to the boiling point of the solvent. It is slightly exothermic and cooling with a water bath is desirable in order that the temperature may not rise above 50° C.

Suitable inert non-aqueous solvents are ethers such as diethyl ether, diisopropyl ether or dioxan, ketones such as acetone or methyl ethyl ketone, and aromatic hydrocarbons such as benzene or toluene, in which the reactants are soluble. Preferred halogen atoms Y are chlorine and bromine. The condensation product is isolated by evaporating the solvent after first removing by filtration the salt which has formed.

Suitable organic bases are tertiary amines, dimethylaniline, triethylamine, and also pyridine or collidine.

The final product is purified by recrystallising it e.g. from an ether.

Depending on the end use, the safener or antidote of the formula I can be used for pretreating seeds of the cultivated plant (dressing of the seeds or seedlings) or it can be added to the soil before or after sowing. However, it cann also be applied pre- or postemergence by itself alone or together with the herbicide. The treatment of the plant or seeds with the safener can therefore in principle be carried out irrespective of the time of application of the phytotoxic chemical. It can, however, also be carried out by simultaneous application of phytotoxic chemical and safener (tank mixture). The pre-emergence treatment includes both treatment of the crop area before sowing (ppi=pre-plant incorporation) and treatment of the crop areas after sowing but before emergence of the plants.

The rates of application of the safener with respect to the herbicide depend largely on the mode of application. Where a field treatment is carried out, either simultaneously as tank mixture or with separate application of herbicide and safener, the ratio of safener to herbicide is in the range from 1:100 to 5:1. Full protective action is usually obtined at a ratio of safener to herbicide of 1:1 to 1:20. When dressing seeds and taking similar specific protective measures, however, much lower amounts of safener are required compared with e.g. the amounts of herbicide later employed per hectare of crop area. For seed dressing, 0.1 to 10 g of safener per kg of seeds are normally required. Full protection is usually obtained with 0.1 to 2 g of safener per gram of seeds. If it is desired to apply the safener shortly before sowing by seed pretreatment, antidote solutions which contain the active ingredient in a concentration of 1 to 10,000 ppm are used. Full protective action will normally be obtained with safener concentrations of 100 to 1000 ppm.

As a rule there is a substantial interval of time between protective measures such as seed dressing and treatment of seedlings with a safener of the formula I and the possible later field treatment with agricultural chemicals. Pretreated seeds and plants can later come in contact with different chemicals in agriculture, horticulture and forestry. Accordingly, the invention relates to plant protection compositions which contain an safener of the formula I as active ingredient, together with conventional carriers. If appropriate, such compositions may be additionally mixed with the chemical from whose effects it is desired to protect the cultivated plant.

Cultivated plants within the scope of this invention are all plants which, in any form, can be harvested (seeds, roots, stalks, tubers, leaves, blossoms) and from which extracts can be obtained (oils, sugar, starch, protein) and which are cultivated for this purpose. These plants comprise e.g. all species of cereals such as wheat, rye, barley, oats and, in particular, rice, sorghum, maize, and also cotton, sugar beet, sugar cane, soybeans, beans, and peas.

The safener can be employed wherever it is desired to protect a cultivated plant of the kind indicated above from the harmful effects of an agricultural chemical. As already mentioned, possible agricultural chemicals are primarily herbicides of the most widely varying compound classes, in particular haloacetanilides and thiocarbamates.

Numerous haloacetanilides whose harmful effects on cultivated plants can be antagonised with the novel oxime ethers of the formula I are known in the art (q.v. German patent applications 2 305 495, 2 328 340, 2 212 268, 2 726 252 and 2 805 757, and U.S. Pat. No. 3,946,044, 4,022,608 and 4,039,314). Such haloacetanilides may be illustrated by the general formula VII

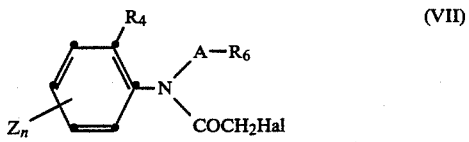 (VII)

wherein Hal is halogen, preferably chlorine or bromine, each of $R_4$ and $R_5$ independently of the other is hydrogen, halogen, lower alkyl, alkoxy, alkylthio, haloalkyl, alkoxyalkyl or alkylthioalkyl, Z is hydrogen, halogen, lower alkyl, alkoxy, alkylthio, haloalkyl, alkoxyalkyl or alkylthioalkyl, which radicals Z are preferably in the 3-position with respect to the nitrogen atom, n is 0 to 3, A is alkylene, preferably methylene, 1,1-ethylene, and 1,2-ethylene which may be substituted by 1 or 2 lower alkyl groups, and $R_6$ is lower alkoxy, hydroxycarbonyl, alkoxycarbonyl, carbamoyl, N-alkylcarbamoyl, N,N-dialkylcarbamoyl, cyano, an unsubstituted or substituted nitrogen-containing heterocyclic radical, alkanoyl, unsubstituted or substituted benzoyl, unsubstituted or substituted 1,3,4-oxadiazol-2-yl, 1,3,4-thiadiazol-2-yl, 1,3,4-triazol-3-yl or 1,3,4-triazol-1-yl.

Typical examples of such haloacetanilides are:
N-ethoxymethyl-N-chloroacetyl-2-ethyl-6-methylaniline
N-chloroacetyl-N-methoxymethyl-2,6-diethylaniline
N-chloroacetyl-N-(2-methoxyethyl)-2,6-dimethylaniline
N-(2-allyloxyethyl)-N-chloroacetyl-2,6-dimethylaniline
N-chloroacetyl-N-(2-propoxyethyl)-2,6-dimethylaniline
N-chloroacetyl-N-(2-isopropoxyethyl)-2,6-dimethylaniline
N-chloroacetyl-N-(2-methoxyethyl)-2-ethyl-6-methylaniline
N-chloroacetyl-N-(methoxyethyl)-2,6-diethylaniline
N-(2-ethoxyethyl)-N-chloroacetyl-2-ethyl-6-methylaniline
N-chloroacetyl-N-(2-methoxy-1-methylethyl)-2-methylaniline
N-chloroacetyl-N-(2-methoxy-1-methylethyl)-2,6-dimethylaniline
N-chloroacetyl-N-(2-methoxy-1-methylethyl)-2,6-diethylaniline
N-chloroacetyl-N-(2-methoxy-1-methylethyl)-2-ethyl-6-methylaniline
N-(2-ethoxyethyl)-N-chloroacetyl-2,6-diethylaniline
N-chloroacetyl-N-(2-n-propoxyethyl)-2-ethyl-6-methylaniline
N-chloroacetyl-N-(2-n-propoxyethyl)-2,6-diethylaniline
N-chloroacetyl-N-(2-isopropoxyethyl)-2-ethyl-6-methylaniline
N-ethoxycarbonylmethyl-N-chloroacetyl-2,6-dimethylaniline
N-ethoxycarbonylmethyl-N-chloroacetyl-2,6-diethylaniline
N-chloroacetyl-N-(2-methoxy-1-methylethyl)-2,6-diethylaniline
N-chloroacetyl-N-(2-methoxy-1-methylethyl)-2-ethyl-6-methylaniline
N-(2-ethoxyethyl)-N-chloroacetyl-2,6-diethylaniline
N-chloroacetyl-N-(2-n-propoxyethyl)-2-ethyl-6-methylaniline
N-chloroacetyl-N-(2-n-propoxyethyl)-2,6-diethylaniline
N-chloroacetyl-N-(2-isopropoxyethyl)-2-ethyl-6-methylaniline
N-ethoxycarbonylmethyl-N-chloroacetyl-2,6-dimethylaniline
N-ethoxycarbonylmethyl-N-chloroacetyl-2,6-diethylaniline
N-chloroacetyl-N-methoxycarbonylmethyl-2,6-dimethylaniline
N-chloroacetyl-N-(2,2-diethoxyethyl)-2,6-dimethylaniline
N-chloroacetyl-N-(2-methoxy-1-methylethyl)-2,3-dimethylaniline
N-(2-ethoxyethyl)-N-chloroacetyl-2-methylaniline
N-chloroacetyl-N-(2-methoxyethyl)-2-methylaniline
N-chloroacetyl-N-(2-methoxy-2-methylethyl)-2,6-dimethylaniline
N-(2-ethoxy-2-methylethyl)-N-chloroacetyl-2-ethyl-6-methylaniline
N-chloroacetyl-N-(1-ethyl-2-methoxyethyl)-2,6-dimethylaniline
N-chloroacetyl-N-(2-methoxyethyl)-2-methoxy-6-methylaniline
N-n-butoxymethyl-N-chloroacetyl-2-tert-butylaniline
N-(2-ethoxyethyl-1-methylethyl)-2,6-dimethylaniline
N-chloroacetyl-N-(2-methoxyethyl)-2-chloro-6-methylaniline
N-(2-ethoxyethyl)-N-chloroacetyl-2-chloro-6-methylaniline
N-(2-ethoxyethyl)-N-chloroacetyl-2,3,6-trimethylaniline
N-chloroacetyl-1-(2-methoxyethyl)-2,3,6-trimethylaniline
N-chloroacetyl-N-cyanomethyl-2,6-dimethylaniline
N-but-3-yn-1-yl-N-chloroacetylaniline
N-chloracetyl-N-propargyl-2-ethyl-6-methylaniline
N-chloracetyl-N-(1,3-dioxolan-2-ylmethyl)-2,6-dimethylaniline
N-chloroacetyl-N-(1,3-dioxolan-2-ylmethyl)-2-ethyl-6-methylaniline
N-chloroacetyl-N-(1,3-dioxan-2-ylmethyl)-2-ethyl-6-methylaniline
N-chloroacetyl-N-(1,3-dioxan-2-ylmethyl)-2-ethyl-6-methylaniline
N-chloroacetyl-N-(2-furanylmethyl)-2,6-dimethylaniline
N-chloroacetyl-N-(2-furanylmethyl)-2-ethyl-6-methylaniline
N-chloroacetyl-N-(2-tetrahydrofuranylmetyl)-2,6-dimethylaniline
N-chloroacetyl-N-(N-propargylcarbamoylmethyl)-2,6-dimethylaniline N-chloroacetyl-N-(N,N-dimethylcarbamoylmethyl)-2,6-dimethylaniline
N-(n-butoxymethyl)-N-chloroacetyl-2,6-diethylaniline
N-(2-n-butoxyethyl)-N-chloroacetyl-2,6-diethylaniline
N-chloroacetyl-N-(2-methoxy-1,2-dimethylethyl)-2,6-dimethylaniline
N-chloroacetyl-N-isopropyl-2,3-dimethylaniline
N-chloroacetyl-N-isopropyl-2-chloroaniline
N-chloroacetyl-N-(1H-pyrazol-2-ylmethyl)-2,6-dimethylaniline
N-chloroacetyl-N-(1H-pyrazol-1-ylmethyl)-2-ethyl-6-methylaniline
N-chloroacetyl-N-(1H-1,2,4-triazol-1-ylmethyl)-2,6-dimethylaniline
N-chloroacetyl-N-(1H-1,2,4-triazol-1-ylmethyl)-2,6-diethylaniline
N-benzoylmethyl-N-chloroacetyl-2,6-dimethylaniline
N-benzoylmethyl-N-chloroacetyl-2-ethyl-6-methylaniline
N-chloroacetyl-N-(5-methyl-1,3,4-oxadiazol-2-yl)-2,6-diethylaniline
N-chloroacetyl-N-(5-methyl-1,3,4-oxadiazol-2-yl)-2-ethyl-6-methylaniline
N-chloroacetyl-N-(5-methyl-1,3,4-oxadiazol-2-yl)-2-tert-butylaniline
N-chloroacetyl-N-(4-chlorobenzoylmethyl)-2,6-dimethylaniline
N-chloroacetyl-N-(1-methyl-5-methylthio-1,3,4-triazol-2-ylmethyl)-2,6-diethylaniline.

Further haloacetanilides whose harmful effects on cultivated plants can be antagonised by the novel oxime ethers of the formula I are listed in R. Wegler, Chemie der Pflanzenschutz- and Schädlingsbekämpfungsmittel, Vol. 8, pp 90–93 and pp. 322–327.

Numerous herbicidal thiocarbamates whose phytotoxic action on cultivated plants can be antagonised by the novel oxime ethers of the formula I are also known (q.v. for example U.S. Pat. Nos. 2,913,327, 3,038,853, 3,175,987, 3,185,720, 3,198,786, 3,582,314 and 3,846,115). The protective action of the novel oxime ethers of the formula I can be utilised particularly when applying thiocarbamates in cereals, rice or sorghum.

The thiocarbamates against whose phytotoxic action cultivated plants such as cereals, rice and sorghum may particularly be protected, have the formulae VIII and IX $$R_7-S-\overset{O}{\underset{\|}{C}}-N\overset{R_8}{\underset{R_9}{\diagdown}} \quad R_7-SO-\overset{O}{\underset{\|}{C}}-N\overset{R_8}{\underset{R_9}{\diagdown}}$$

(VIII)  (IX)

wherein $R_7$ is lower alkyl, alkenyl, chloroallyl, dichloroallyl, trichloroallyl, benzyl or 4-chlorobenzyl, $R_8$ is $C_2$–$C_4$ alkyl and $R_9$ is $C_2$–$C_4$ alkyl or cyclohexyl, and $R_8$ and $R_9$ together with the nitrogen atom to which they are attached can form a hexahydro-1H-azepine, decahydroquinoline or 2-methyldecahydroquinoline ring.

Typical individual representatives of such thiocarbamates are:
S-ethyl-N,N-dipropylthiocarbamate
S-ethyl-N,N-diisopropylthiocarbamate
S-2,3-dichloroallyl-N,N-diisopropylthiocarbamate
S-propyl-N-butyl-N-ethylthiocarbamate
S-2,3,3-trichloroallyl-N,N-diisopropylthiocarbamate
S-propyl-N,N-dipropylthiocarbamate
S-ethyl-N-ethyl-N-cyclohexylthiocarbamate
S-ethyl-N-hexahydro-1H-azepine-1-carbothioate
S-isopropyl-N,N-hexamethylene-thiocarbamate
S-(p-chlorobenzyl)-N,N-diethylthiocarbamate
N-ethylthiocarbonyl-cis-decahydroquinoline
N-propylthiocarbonyl-decahydroquinaldine
S-ethyl-N,N-bis(n-butyl)-thiocarbamate
S-tert-butyl-N,N-bis(n-propyl)-thiocarbamate.

In addition to the chloroacetanilides and thiocarbamates, other classes of herbicides are also suitable, for example:

Triazines and triazinones: 2,4-bis(aminopropylamino)-6-methylthio-1,3,5-triazine ("prometryn"), 2,4-bis(ethylamino)-6-methylthio-1,3,5-triazine ("symetrin"), 2-(1',2'-dimethylpropylamino)-4-ethylamino-6-methylthio-1,3,5-triazine ("dimethametryn"), 4-amino-6-tert-butyl-4,5-dihydro-3-methylthio-1,2,4-triazin-5-one ("metribuzin"), 2-chloro-4-ethylamino-6-isopropylamino-1,3,5-triazine ("atrazin"), 2-chloro-4,6-bis(ethylamino)-1,3,5-triazine ("simazin"), 2-tert-butylamino-4-chloro-6-ethylamino-1,3,5-triazine ("terbuthylazin"), 2-tert-butylamino-4-ethylamino-6-methoxy-1,3,5-triazine ("terbumeton"), 2-tert-butylamino-4-ethylamino-6-methylthio-1,3,5-triazine ("terbutryn"), 2-ethylamino-4-isopropylamino-6-methylthio-1,3,5-triazine ("ametryn");

Ureas: 1-(benzothiazol-2-yl)-1,3-dimethylurea; phenylureas such as 3-(3-chloro-p-tolyl)-1,1-dimethylurea ("chlorotoluron"), 1,1-dimethyl-3-(α,α,α-trifluoro-m-tolyl)urea ("fluormeturon"), 3-(4-bromo-3-chlorophenyl)-1-methoxy-1-methylurea ("chlorbromuron"), 3-(4-bromophenyl)-1-methoxy-1-methylurea ("metobromuron"), 3-(3,4-dichlorophenyl)-1-methoxy-1-methylurea ("linuron"), 3-(4-chlorophenyl)-1-methoxy-1-methylurea ("monolinuron"), 3-(3,4-dichlorophenyl)-1,1-dimethylurea ("diuron"), 3-(4-chlorophenyl)-1,1-dimethylurea ("monuron"), 3-(3-chloro-4-methoxyphenyl)-1,1-dimethylurea ("metoxuron"); sulfonylureas, e.g. N-(2-chlorophenylsulfonyl)-N'-(4-methoxy)-6-methyl-1,3,5-triazin-2-yl)urea, N-(2-methoxycarbonylphenylsulfonyl)-N'-(4,6-dimethylpyridin-2-yl)urea, N-[2-(2-butenyloxy)phenylsulfonyl]-N'-(4-methoxy-6-methyl-1,3,5-triazin-2-yl)urea, as well as the sulfonylureas listed in European patent publications 44808 and 44809;

Chloroacetamides: N-[1-isopropyl-2-methylpropan-1-yl(1)]-N-(2'-methoxyethyl)-chloroacetamide.

Diphenyl ethers and nitrodiphenyl ethers: 2,4-dichlorophenyl-4'-nitrophenyl ether ("nitrofen"), 2-chloro-1-(3'-ethoxy-4'-nitrophenoxy)-4-trifluoromethylbenzene ("oxyfluorfen"), 2',4'-dichlorophenyl-3-methoxy-4-nitrophenyl ether ("chlormethoxynil"), methyl-2-[4'-(2'',4''-dichlorophenoxy)phenoxy]propionate, N-(2'phenoxyethyl)-2-[5'(2''-chloro-4''[(trifluoromethylphenoxy)phenoxy]propionamide, 2-methoxyethyl]2-[2-nitro-5-(2-chloro-4-trifluoromethylphenoxy)-phenoxy]propionate; nitrophenyl 2-chloro-4-trifluoromethylphenyl-3'-oxazolin-2'-yl-4'-nitrophenyl ether;

Benzoic acid derivatives: methyl-5-(2',4'-dichlorophenoxy)-2-nitrobenzoate ("bifenox"), 5-(2-chloro-4'-trifluoromethylphenoxy)-2-nitrobenzoic acid ("acifluorfen"), 2,6-dichlorobenzonitrile ("dichlobenil").

Nitroanilines: 2,6-dinitro-N,N-dipropyl-4-trifluoromethylaniline ("trifluralin"), N(1-'ethylpropyl)-2,6-dinitro-3,4-xylidine ("pendimethalin").

Oxadiazolones: 5-tert-butyl-3(2',4'-dichloro-5'-isopropoxyphenyl)-1,3,4-oxadiazol-2-one ("oxadiazon").

Phosphates: S-2-methylpiperidinocarbonylmethyl-O,O-dipropylphosphorodithioate ("piperophos").

Pyrazoles: 1,3-dimethyl-4-(2',4'-dichlorobenzoyl)-5-(4'-tolylsolfonyloxy)pyrazole.

Other suitable herbicides are α-(phenoxyphenoxy)-propionic acid derivatives and α-(pyridyl-2-oxyphenoxy)propionic acid derivatives.

The concentration of safener, provided it is not used for seed dressing, varies from about 0.01 to 5 parts by weight per part by weight of herbicide. The most suitable ratio for achieving optimum effects in the particular cultivated plant is determined from case to case, i.e. depending on the type of herbicide employed.

The compounds of formula I are used in unmodified form or, preferably, as compositions, together with the adjuvants conventionally employed in formulation technology, and are therefore formulated in known manner to emulsifiable concentrates, directly sprayable or dilutable solutions, dilute emulsions, wettable powders, soluble powders, dusts, granulates, and also encapsulations in e.g. polymeric substances. As with the nature of the compositions, the methods of application such as spraying, scattering or pouring are chosen in accordance with the intended objectives and the prevailing circumstances. The formulations, i.e. the compositions containing the compound of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts or higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethylanolamine salts of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp. Ridgewood, N.J., 1981; H. Stache, "Tensid-Taschenbuch", 2nd Edition, C. Hanser Verlag, Munich & Vienna, 1981; M. and J. Ash, "Encyclopedia of Surfactants", Vol. I–III, Chemical Publishing Co., New York, 1980–81.

The herbicidal compositions usually contain 0.1 to 95%, preferably 0.1 to 80%, of a compound of the formula I, 1 to 99.9%, of a solid or liquid adjuvant, and 0 to 25%, preferably 0.1 to 25%, of a surfactant.

Preferred formulations are composed in particular of the following constituents (%=percentage by weight):

| Emulsifiable concentrates | |
|---|---|
| active ingredient: | 1 to 20%, preferably 5 to 10% |
| surfactant: | 5 to 30%, preferably 10 to 20% |
| liquid carrier: | 50 to 94%, preferably 70 to 85% |
| Dusts | |
| active ingredient: | 0.1 to 10%, preferably 0.1 to 1% |
| solid carrier: | 99.9 to 90%, preferably 99.9 to 99% |
| Suspension concentrates | |
| active ingredient: | 5 to 75%, preferably 10 to 50% |
| water: | 94 to 25%, preferably 90 to 30% |
| surfactant: | 1 to 40%, preferably 2 to 30% |
| Wettable powders | |
| active ingredient: | 0.5 to 90%, preferably 1 to 80% |
| surfactant: | 0.5 to 20%, preferably 1 to 15% |
| solid carrier: | 5 to 95%, preferably 15 to 90% |
| Granulates | |
| active ingredient: | 0.5 to 30%, preferably 3 to 15% |
| solid carrier: | 99.5 to 70%, preferably 97 to 85%. |

Whereas commercial products will be preferably formulated as concentrates, the end user will normally employ dilute formulations. The formulations can be diluted to a concentration as low as 0.001% The rates of application are normally from 0.01 to 10 kg a.i./ha, preferably from 0.025 to 5 kg a.i./ha.

The compositions may also contain further ingredients such as stabilisers, antifoams, viscosity regulators, binders, tackifiers, as well as fertilisers and other compounds for obtaining special effects.

The invention is illustrated by the following Examples in which the pressures are indicated in millibars (mb).

EXAMPLE 1

Preparation of diethyl chloroacetylaminomethylphosphonate

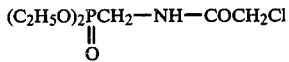

With stirring, 32 ml (0.4 mole) of chloroacetyl chloride are slowly added dropwise to a solution of 66.4 g (0.4 mole) of diethyl aminomethanephosphonate and 56 ml (0.4 mole) of triethylamine in 600 ml of benzene. The reaction is exothermic and the temperature is kept at 40° C. by cooling. After completion of the dropwise addition the reaction mixture is stirred for 1 hour at room temperature. Precipitated triethylamine hydrochloride is removed by filtration and the filtrate is concentrated in vacuo. The residual pale brown oil is crystallised from ether, affording 88 g of the above ester which has a melting point of 62°-65° C.

EXAMPLE 2

Preparation of diisopropyl chloroacetylaminomethylphosphonate

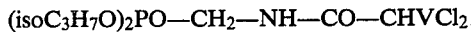

15 g of diisopropyl aminomethanephosphonate and 11.2 ml of triethylamine are dissolved in 200 ml of benzene. With stirring, 7.8 ml of dichloroacetyl chloride are added dropwise and the temperature rises to 41° C. When the dropwise addition is complete, the reaction mixture is stirred for 1 hour at room temperature. The precipitated triethylamine hydrochloride is subsequently removed by filtration and the filtrate is concentrated in vacuo and the residual oil is crystalised from ether. Recrystallisation from diisopropyl ether affords 18.7 g of the above ester, which has a melting point of 79°.81° C.:

EXAMPLE 3

Preparation of diethyl chloroacetylamino-2-propylphosphonate

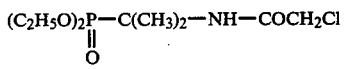

A solution of 7.7 ml of triethylamine and 9.4 21 of chloroacetic anhydride in 50 ml of ether is added at 5°-10° C. to a solution of 9.8 g of diethyl 2-aminopropyl-2-phosphonate in 50 ml of ether. The reaction mixture is then stirred for 2 hours at 20° C. The yellow suspension is extracted with three 50 ml portions of water and the organic phase is dried over sodium sulfate, filtered and concentrated. Yield: 4.8 g of final product which melts at 93°-95° C. after recrystallisation from diisopropyl ether. Extraction of the aqueous phase with ether affords another 4.6 g of final product, which also melts at 93°-95° C. Yield: 8.9 g (65% of theory).

The following compounds are obtained by procedures analogous to those described in the foregoing Examples:

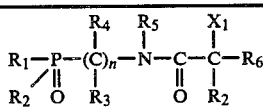

| No. | $R_1 R_2$ | $-[C(R_3)R_4]_n-$ | $R_5$ | $-C(X_1)(X_2)R_6$ | Physical data °C. |
|---|---|---|---|---|---|
| 1 | $(C_2H_5O)_2$ | $CH_2$ | H | $CH_2Cl$ | m.p. 62-65 |
| 2 | $(isoC_3H_7O)_2$ | $CH_2$ | H | $CHCl_2$ | m.p. 79-81 |
| 3 | $(C_2H_5O)_2$ | $C(CH_3)_2$ | H | $CH_2Cl$ | m.p. 93-95 |
| 4 | $(C_2H_5O)_2$ | $CH_2$ | H | $CHCl_2$ | b.p. 174-176/p. 1 mbar |
| 5 | $(isoC_3H_7O)_2$ | $CH_2$ | H | $CH_2Cl$ | m.p. 70-71 |
| 6 | $(C_2H_5O)_2$ | $CH_2$ | H | $CH_2Br$ | m.p. 88-90 |
| 7 | $(isoC_3H_7O)_2$ | $CH_2$ | H | $CH_2Br$ | m.p. 85-88 |
| 8 | $(C_2H_5O)_2$ | $(C_2H_5O)_2P(O)CH$ | H | $CH_2Cl$ | m.p. 54-57 |
| 9 | $(C_2H_5O)_2$ | cyclohexylene | H | $CH_2Cl$ | m.p. 80-100 |
| 10 | $(C_2H_5O)_2$ | $C(CH_3)_2$ | benzyl | $CH_2Cl$ | oil |
| 11 | $(C_2H_5O)_2$ | $(C_2H_5O)_2P(O)CH$ | H | $CHCl_2$ | m.p. 78-82 |
| 12 | $(isoC_3H_7O)_2$ | $CH_2$ | $CH_3$ | $CH_2Cl$ | orange oil |

-continued $$R_1-\underset{\underset{R_2}{\|}}{\overset{O}{P}}-(\overset{R_4}{\underset{R_3}{C}})_n-\overset{R_5}{\underset{\|}{N}}-\overset{}{\underset{O}{C}}-\overset{X_1}{\underset{R_2}{C}}-R_6$$

| No. | $R_1$ $R_2$ | $-[C(R_3)R_4]_n-$ | $R_5$ | $-C(X_1)(X_2)R_6$ | Physical data °C. |
|---|---|---|---|---|---|
| 13 | (isoC$_3$H$_7$O)$_2$ | CH$_2$ | CH(CH$_3$)$_2$ | CH$_2$Cl | |
| 14 | (isoC$_3$H$_7$O)$_2$ | CH$_2$ | cyclopropyl | CH$_2$Cl | |
| 15 | (isoC$_3$H$_7$O)$_2$ | CH$_2$ | CH$_2$CH=CH$_2$ | CH$_2$Cl | oil |
| 16 | (isoC$_3$H$_7$O)$_2$ | CH$_2$ | benzyl | CH$_2$Cl | |
| 17 | (isoC$_3$H$_7$O)$_2$ | CH$_2$ | CH$_3$ | CHCl$_2$ | orange oil |
| 18 | (isoC$_3$H$_7$O)$_2$ | CH$_2$ | CH(CH$_3$)$_2$ | CHCl$_2$ | |
| 19 | (isoC$_3$H$_7$O)$_2$ | CH$_2$ | cyclopropyl | CHCl$_2$ | |
| 20 | (isoC$_3$H$_7$O)$_2$ | CH$_2$ | CH$_2$CH=CH$_2$ | CHCl$_2$ | oil |
| 21 | (isoC$_3$H$_7$O)$_2$ | CH$_2$ | benzyl | CHCl$_2$ | |
| 22 | (nC$_4$H$_9$O)$_2$ | CH$_2$ | CH$_3$ | CH$_2$Cl | |
| 23 | (nC$_4$H$_9$O)$_2$ | CH$_2$ | CH(CH$_3$)$_2$ | CH$_2$Cl | |
| 24 | (nC$_H$O)$_2$ | CH$_2$ | cyclopropyl | CH$_2$Cl | |
| 25 | (nC$_4$H$_9$O)$_2$ | CH$_2$ | CH$_2$CH=CH$_2$ | CH$_2$Cl | |
| 26 | (nC$_4$H$_9$O)$_2$ | CH$_2$ | benzyl | CH$_2$Cl | |
| 27 | (nC$_4$H$_9$O)$_2$ | CH$_2$ | CH$_3$ | CHCl$_2$ | |
| 28 | (nC$_4$H$_9$O)$_2$ | CH$_2$ | C(CH$_3$)$_2$ | CHCl$_2$ | |
| 29 | (nC$_4$H$_9$O)$_2$ | CH$_2$ | cyclopropyl | CHCl$_2$ | |
| 30 | (nC$_4$H$_9$O)$_2$ | CH$_2$ | CH$_2$CH=CH$_2$ | CHCl$_2$ | |
| 31 | (nC$_4$H$_9$O)$_2$ | CH$_2$ | benzyl | CHCl$_2$ | |
| 32 | (CH$_3$O)$_2$ | cyclopentylene | C$_4$H$_9$n | CH$_2$Cl | |
| 33 | CH$_3$O, C$_2$H$_5$O | cyclohexylene | C$_4$H$_9$n | CH$_2$Cl | |
| 34 | (C$_2$H$_5$O)$_2$ | cycloheptylene | C$_4$H$_9$ | CH$_2$Cl | |
| 35 | (C$_2$H$_5$O)$_2$ | α-perhydronaphthylene | C$_3$H$_7$n | CH$_2$Cl | |
| 36 | CH$_3$O CH$_3$ | cyclopentylene | CH$_3$ | CH$_2$Cl | |
| 37 | C$_2$H$_5$ CH$_3$ | cyclopropylene | CH$_3$ | CH$_2$Cl | |
| 38 | (CH$_3$)$_2$ | cycloheptylene | CH$_3$ | CH$_2$Cl | |
| 39 | (C$_2$H$_5$)$_2$ | cyclohexylene | CH$_3$ | CH$_2$Cl | |
| 40 | CH$_3$, C$_2$H$_5$O | cyclopentylene | CH$_3$ | CH$_2$Cl | |
| 41 | CH$_3$, nC$_3$H$_7$O | cyclopentylene | CH$_3$ | CH$_2$Cl | |
| 42 | (isoC$_3$H$_7$O)$_2$ | C(H)CH$_3$ | benzyl | CH$_2$Cl | |
| 43 | (isoC$_3$H$_7$O)$_2$ | C(CH$_3$)$_2$ | benzyl | CH$_2$Cl | |
| 44 | CH$_3$, C$_2$H$_5$O | C(CH$_3$)cyclopropylene | H | CH$_2$Cl | |
| 45 | CH$_3$, C$_2$H$_5$O | C(CH$_3$)C$_2$H$_5$ | H | CH$_2$Cl | |
| 46 | CH$_3$, nC$_4$H$_9$O | C(CH$_3$)C$_2$H$_5$ | H | CH$_2$Cl | |
| 47 | CH$_3$, C$_2$H$_5$O | C(CH$_3$)$_2$ | H | CH$_2$Cl | |
| 48 | C$_2$H$_5$, C$_2$H$_5$O | C(CH$_3$)$_2$ | benzyl | CH$_2$Cl | |
| 49 | C$_2$H$_5$, C$_2$H$_5$O | C(CH$_3$)$_2$ | H | CH$_2$Cl | |
| 50 | (C$_2$H$_5$)$_2$ | C(CH$_3$)$_2$ | benzyl | CH$_2$Cl | |
| 51 | (CH$_3$)$_2$ | CH$_2$ | H | CH$_2$Cl | |
| 52 | (CH$_3$)$_2$ | CH$_2$ | H | CHCl$_2$ | |
| 53 | (C$_2$H$_5$)$_2$ | CH$_2$ | H | CHCl$_2$ | |
| 54 | CH$_3$, C$_2$H$_5$ | CH$_2$ | H | CHCl$_2$ | |
| 55 | CH$_3$, i-C$_4$H$_9$O | C(CH$_3$)(C$_2$H$_5$) | H | CHCl$_2$ | yellowish brown |
| 56 | H, C$_2$H$_5$O | CH$_2$CH$_2$ | benzyl | CH$_2$Cl | brown resin |
| 57 | H, C$_2$H$_5$O | CH$_2$CH$_2$ | benzyl | CHCl$_2$ | brown resin |
| 58 | (isoC$_3$H$_7$O)$_2$ | CH$_2$ | CH$_2$CH=CH$_2$ | CH$_2$I | oil |
| 59 | (C$_2$H$_5$O)$_2$ | CH$_2$ | CH(CH$_3$)$_2$ | CH$_2$Cl | oil |
| 60 | (C$_2$H$_5$O)$_2$ | CH$_2$ | CH(CH$_3$)$_2$ | CHCl$_2$ | m.p. 84-86 |
| 61 | (C$_2$H)$_2$ | CH$_2$ | cyclopropyl | CH$_2$Cl | oil |
| 62 | (C$_2$H$_5$O)$_2$ | CH$_2$ | cyclopropyl | CHCl$_2$ | oil |
| 63 | (C$_2$H$_5$O)$_2$ | CH$_2$ | CH$_2$CH=CH$_2$ | CH$_2$Cl | oil |
| 64 | (CH$_3$O)$_2$ | CH$_2$ | H | CH$_2$Cl | n$_D^{20}$ 1.4710 |
| 65 | (C$_2$H$_5$O)$_2$ | CH$_2$ | H | CHClCH$_3$ | n$_D^{20}$ 1.4630 |
| 66 | (C$_2$H$_5$O)$_2$ | CH$_2$ | H | CHClCH$_2$Cl | n$_D^{20}$ 1.4775 |
| 67 | (C$_2$H$_5$O)$_2$ | CH$_2$ | H | CH$_2$CH$_2$Cl | n$_D^{20}$ 1.4709 |
| 68 | (C$_2$H$_5$O)$_2$ | CH$_2$ | H | CH$_2$CH$_2$CH$_2$Cl | n$_D^{20}$ 1.4720 |
| 69 | (C$_2$H$_5$O)$_2$ | CH$_2$ | benzyl | CH$_2$Cl | n$_D^{20}$ 1.5136 |
| 70 | (C$_2$H$_5$O)$_2$ | CH$_2$ | benzyl | CHCl$_2$ | m.p. 56-60 |
| 71 | (C$_2$H$_5$O)$_2$ | CH$_2$ | CH$_2$CF$_3$ | CH$_2$Cl | n$_D^{20}$ 1.4222 |
| 72 | (C$_2$H$_5$O)$_2$ | CH$_2$ | CH$_2$CF$_3$ | CHCl$_2$ | n$_D^{20}$ 1.4397 |
| 73 | (isoC$_3$H$_7$O)$_2$ | CH$_2$ | H | CHClCH$_3$ | n$_D^{20}$ 1.4563 |
| 74 | (isoC$_3$H$_7$O)$_2$ | CH$_2$ | H | CHClCH$_2$Cl | n$_D^{20}$ 1.4696 |
| 75 | (isoC$_3$H$_7$O)$_2$ | CH$_2$ | H | CH$_2$CH$_2$Cl | n$_D^{20}$ 1.4593 |
| 76 | (isoC$_3$H$_7$O)$_2$ | CH$_2$ | H | CH$_2$CH$_2$CH$_2$Cl | n$_D^{20}$ 1.4596 |
| 77 | (C$_2$H$_5$O)$_2$ | (C$_2$H$_5$)$_2$POCH= | H | CHClCH$_3$ | n$_D^{20}$ 1.4612 |
| 78 | (C$_2$H$_5$O)$_2$ | (C$_2$H$_5$)$_2$POCH= | H | CHClCH$_2$Cl | n$_D^{20}$ 1.4691 |
| 79 | (C$_2$H$_5$O)$_2$ | (C$_2$H$_5$O)$_2$POCH= | H | CH$_2$CH$_2$Cl | m.p. 71-74 |
| 80 | (C$_2$H$_5$O)$_2$ | (C$_2$H$_5$O)$_2$POCH= | H | CH$_2$CH$_2$CH$_2$Cl | n$_D^{20}$ 1.4711 |
| 81 | (C$_2$H$_5$O)$_2$ | CH$_2$CH$_2$ | H | CH$_2$Cl | oil |
| 82 | (C$_2$H$_5$O)$_2$ | CH$_2$CH$_2$ | H | CHCL$_2$ | n$_D^{20}$ 1.4754 |
| 83 | CH$_3$, isoC$_3$H$_7$O | CH$_2$ | H | CH$_2$Cl | m.p. 67-69 |
| 84 | CH$_3$, isoC$_3$H$_7$O | CH$_2$ | H | CHCl$_2$ | m.p. 105-107 |
| 85 | (nC$_4$H$_9$O)$_2$ | cycloheptylene | | CH$_2$Cl | oil |
| 86 | (nC$_4$H$_9$O)$_2$ | cycloheptylene | | | oil |
| 87 | CH$_3$, C$_2$H$_5$O | CH$_2$ | H | CH$_2$Cl | n$_D^{20}$ 1.4878 |

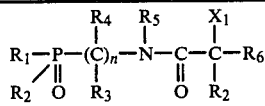

| No. | R₁ R₂ | —[C(R₃)R₄]ₙ— | R₅ | —C(X₁)(X₂)R₆ | Physical data °C. |
|---|---|---|---|---|---|
| 88 | CH₃, C₂H₅O | CH₂ | H | CHCl₂ | $n_D^{20}$ 1.4907 |
| 89 | (isoC₃H₇O)₂ | cyclopropylene | H | CH₂Cl | m.p. 84–85 |
| 90 | (isoC₃H₇O)₂ | cyclopropylene | H | CHCl₂ | m.p. 96–97 |
| 91 | (C₂H₅O)₂ | CH₂ | H | CCl=CCl₂ | oil |
| 92 | (C₂H₅O)₂ | CH₂ | H | CHClCH₃ | oil |
| 93 | (C₂H₅O)₂ | CH₂ | H | CHClCH₂ | oil |
| 94 | (C₂H₅O)₂ | CH₂ | H | CCl=CCl₂ | oil |
| 95 | (HO)² | cyclopropylene | H | CHCl² | |

EXAMPLE 4

Formulation Examples for compounds of the formula I or mixtures thereof with herbicides

| (a) Wettable powders | (a) | (b) | (c) |
|---|---|---|---|
| Compound of formula I | 20% | 60% | 0.5% |
| sodium lignosulfonate | 5% | 5% | 5% |
| sodium laurylsulfate | 3% | — | — |
| sodium diisobutylnaphahalene-sulfonate | — | 6% | 6% |
| octylphenol polyethylene glycol ether (7–8 moles of ethylene oxide) | — | 2% | 2% |
| highly dispersed silicid acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrates | (a) | (b) |
|---|---|---|
| Compound of formula I | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| Compound of formula I | 0.1% | 1% |
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
|---|---|---|
| Compound of formula I | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| Compound of formula | 3% |
| polyethylene glycol 200 | 2% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| Compound of formula I | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| Compound of formula I | 5% |
| isopropylamine | 1% |
| octylphenol polyethylene glycol ether (78 moles of ethylene oxide) | 3% |
| water | 91% |

BIOLOGICAL EXAMPLES

The ability of the compounds of formula I to protect cultivated plants from the phytotoxic effects of potent herbicides can be inferred from the following Examples. The compounds of formula I are referred to as safeners in the test procedures.

EXAMPLE 5

Test with herbicide and safener in maize. Preemergence application of herbicide and safener as tank mixture.

Plastic containers measuring 25 cm × 17 cm × 12 cm are filled with sandy loam and LG 5 maize seeds are sown therein. After the seeds have been covered, a dilute solution of the safener to be tested and the herbicide is sprayed as tank mixture onto the surface of the soil. The protective action of the safener is evaluated (in %) 21 days after application. Plants treated with herbicide alone (no protective action) and completely untreated control plants (100% protective action) are used for reference purposes. The results are reported below.

| Herbicide: N—chloroacetyl-N—(2-methoxy-1-methylethyl)-2,6-dimethyl-aniline | | | |
|---|---|---|---|
| Safener No. | kg./ha | Herbicide kg/ha | Relative protective action in % |
| 1 | 3 | 6 | 63 |
| 1 | 1.5 | 6 | 75 |
| 1 | 0.75 | 6 | 63 |
| 1 | 2 | 4 | 50 |
| 1 | 1 | 4 | 63 |
| 1 | 0.5 | 4 | 50 |
| 4 | 3 | 6 | 50 |
| 4 | 1.5 | 6 | 63 |
| 4 | 0.75 | 6 | 50 |
| 4 | 2 | 4 | 50 |
| 4 | 1 | 4 | 38 |
| 4 | 0.5 | 4 | 50 |

What is claimed is:

1. A composition for protecting cereal crops from the phytotoxic effect of haloacetatanilide herbicides, which composition contains as a safener component a haloacylaminoalkylphosphonate of the formula

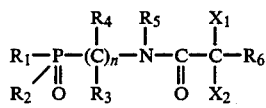

wherein
$R_1$ and $R_2$ are each $C_1$-$C_4$alkoxy, $C_2$-$C_4$alkenyloxy, $C_2$-$C_4$-alkynyloxy, $C_1$-$C_4$haloalkoxy, $C_2$-$C_8$alkoxyalkoxy or $C_1$-$C_4$cyanoalkoxy,
$R_3$ and $R_4$ are each independently hydrogen, $C_1$-$C_4$alkyl or $R_4$ is also a radical

$R_3$ and $R_4$ both taken together with the carbon atom to which they are attached are also a $C_3$-$C_{11}$cycloalkyl radical, $R_5$ is hydrogen, $C_1$-$C_4$alkyl, $C_3$-$C_7$cycloalkyl, $C_2$-$C_4$alkenyl, $C_2$-$C_4$alkynyl, $C_2$-$C_8$alkoxyalkyl, $C_1$-$C_4$haloalkyl or aralkyl, $R_6$ is hydrogen or $C_1$-$C_4$alkyl,
$X_1$ and $X_2$ are each independently halogen or $X_1$ is also hydrogen, and
n is 1, 2 or 3
together with an inert carrier.

2. A composition according to claim 1, wherein each of $R_1$ and $R_2$ is $C_1$-$C_4$alkoxy, each of $R_3$ and $R_4$ is hydrogen or methyl, $R_5$ is hydrogen, $C_1$-$C_4$alkyl or benzyl, $R_6$ is hydrogen, each of $X_1$ and $X_2$ is chlorine or one of $X_1$ and $X_2$ is also hydrogen, and n is 1.

3. A composition according to claim 1, wherein the halocylaminoalkylphosphonate is diethyl chloroacetylaminomethylphosphonate.

4. A composition according to claim 1, wherein the haloacylaminoalkylphosphonate is diethyl dichloroacetylaminoethylphosphonate.

5. A method of selectively controlling weeds in cereal crops, which method comprises treating said crops or the crop area (a) with an effective amount of haloacetanilide herbicide of the formula

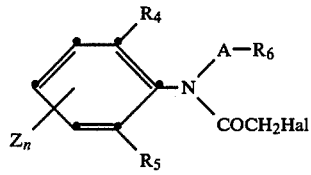

wherein Hal is halogen each of $R_4$ and $R_5$ independently of the other is hydrogen, halogen, $C_1$-$C_4$alkyl or $C_1$-$C_4$alkoxy, n is zero, A is methylene, 1,1-ethylene or 1,2-ethylene which may be substituted by 1 or 2 $C_1$-$C_4$alkyl groups and $R_6$ is $C_1$-$C_4$alkoxyhydroxycarbonyl or $C_1$-$C_4$alkoxycarbonyl and (b) with an effective amount of a haloacylaminoalkyl phosphonate according to claim 1 as safener component.

6. A method of protecting cereal crops from the harmful effects of halo acetanilide herbicides, which comprises applying to said crops to the locus thereof an effective amount of a haloacylaminoalkylphosphonate according to claim 1 as safener component.

7. A method of protecting crops of cereals from damage caused by haloacetanilide herbicides, which comprises applying to said crops an effective amount of a haloacylaminoalkylphosphonate according to claim 1 as safener component.

8. A method of protecting cereal crops from the harmful effects of haloacetanilide herbicides, which comprises
(a) treating the crop area of said plants before or during application of the herbicide or
(b) treating the seeds or seedlings of said plants or the plants themselves with an effective amount of a haloacylaminoalkylphosphonate according to claim 1 as safener component.

9. Seeds of cereal plants which have been treated with an effective amount of a haloacylaminoalkylphosphonate according to claim 1 as safener component.

10. The composition of claim 1 which further contains as herbicide N-chloroacetyl-N-(2-methoxy-1-methylethyl)-2,6-dimethylaniline.

11. The composition of claim 7 wherein the cereal crop is maize or sorghum.

* * * * *